United States Patent [19]

Gobbini et al.

[11] Patent Number: 5,731,345
[45] Date of Patent: Mar. 24, 1998

[54] SECO-D STEROIDS ACTIVE ON THE CARDIOVASCULAR SYSTEM AND PHARMACEUTICAL COMPOSITIONS CONTAINING SAME

[75] Inventors: Mauro Gobbini, Mercallo; Patrizia Ferrari, Varese; Piero Melloni, Bresso; Marco Torri, Rho, all of Italy

[73] Assignee: Sigma-Tau Industrie Farmaceutiche Riunite S.p.A, Rome, Italy

[21] Appl. No.: 632,124

[22] Filed: Apr. 15, 1996

[30] Foreign Application Priority Data

May 11, 1995 [IT] Italy .................. RM95A0303

[51] Int. Cl.$^6$ .................. A61K 31/365; A61K 31/34; C07D 307/58; C07D 307/46
[52] U.S. Cl. .................. 514/461; 514/473; 549/321; 549/323; 549/499; 549/502
[58] Field of Search .................. 549/321, 323, 549/499, 502; 514/461, 473

[56] References Cited

PUBLICATIONS

Cohnen et. al., Liebigs Ann. Chem., pp. 908–913, 1982.

Primary Examiner—Bernard Dentz
Attorney, Agent, or Firm—Oblon, Spivak, McClelland, Maier & Neustadt, P.C.

[57] ABSTRACT

Seco-D steroid derivatives having the formula

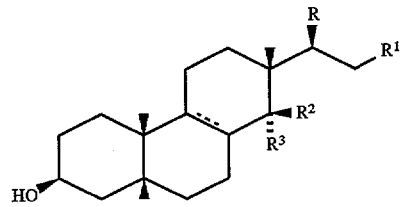

wherein R, $R^1$, $R^2$ and $R^3$ have the meanings specified in the specification, useful as cardiovascular agents and pharmaceutical compositions containing same, are disclosed.

3 Claims, No Drawings

SECO-D STEROIDS ACTIVE ON THE CARDIOVASCULAR SYSTEM AND PHARMACEUTICAL COMPOSITIONS CONTAINING SAME

The present invention relates to novel seco-D steroid derivatives active on the cardiovascular system and pharmaceutical compositions containing same for the treatment of cardiovascular disorders such as heart failure and hypertension.

Digitalis products such as digoxin, oubain and digitoxigenin are natural compounds whose activity on the cardiovascular system has long since been known. This activity has been mainly attributed to these compounds ability in inhibiting $Na^+$, $K^+$-ATPase (Repke K. R. H. Schönfeld W. (1984); $Na^+/K^+$-ATPase as the digitalis receptor; Trends Pharmacol. Sci. 5: 393–397).

The cis junction between the A/B and the C/D rings of the steroid skeleton is the typical configuration of such derivatives and the one which determines the spatial shape of the digitalis compounds (Thomas R., Gray P., Andrews J. (1990); Digitalis: its mode of action, receptor, and structure-activity relationships; Adv. Drugs Res. 19: 312–562).

Although the compounds claimed herein lack the D-ring of the steroid skeleton and, hence, do not comply with the afore-said structural prerequisite, they surprisingly exhibit good affinity for the $Na^+$, $K^+$-ATPase receptor site and are active on the cardiovascular system.

The compounds of the present invention have the following general formula (I)

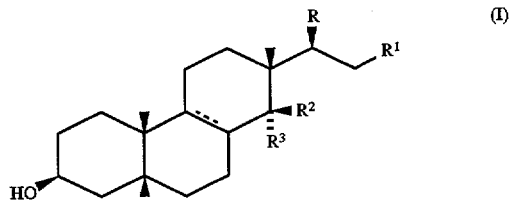

wherein:
R is 3-furyl or 2,5-dihydro-5-oxo-3-furyl;
when R is 3-furyl
the symbol ----- represents a single bond;
$R^1$ is methyl or hydroxymethyl;
$R^2$ and $R^3$ are OH and H respectively, or taken together form a keto group;
with the proviso that when $R^2$ and $R^3$ taken together form a keto group, $R^1$ is methyl;
when R is 2,5-dihydro-5-oxo-3-furyl
the symbol ----- represents either a single or a double bond;
$R^1$ is methyl, cyano or CH=N〜$R^4$;
$R^2$ and $R^3$ have the above-specified meaning;
with the proviso that when $R^1$ is CH=N〜$R^4$, $R^2$ and $R^3$ taken together form a keto group;
with the proviso that when the symbol ----- represents a double bond, $R^1$ is methyl, and $R^2$, $R^3$ taken together form a keto group;
the symbol 〜 represents either the Z or the E isomer;
$R^4$ is NHC(=NH)$NR^5R^6$ or $OR^7$;
wherein
$R^5$, $R^6$, equal or different, are H or $C_1$–$C_4$ alkyl; or $R^5$ and $R^6$ taken together can possibly form, with the heteroatom they are linked to, a five- or six-membered mono-heterocyclic ring;
$R^7$ is H, $CH_3$ or $C_2$–$C_6$ alkyl, unsubstituted or substituted by $NR^8R^9$;
wherein $R^8$ and $R^9$, equal or different, are H or $C_1$–$C_4$ alkyl.

Should the compounds of formula (I) present themselves as distinct tautomeric forms, it should be understood that the foregoing formula also encompasses such forms. The formula encompasses both Z and E isomers as well as mixtures thereof, the metabolites and the metabolic precursors of the compounds of formula (I).

Also encompassed within the scope of the present invention are the pharmacologically acceptable salts of the compounds of formula (I). By pharmacologically acceptable salts are meant those salts which retain the biological activity of the unsalified parent compound and are derived from such known pharmacologically acceptable acids such as e.g. hydrochloric, hydrobromic, sulfuric, phosphoric, fumaric, succinic, ossalic, malic, tartaric, maleic, citric, methanesulfonic or benzoic acid and others still which will be readily apparent to the average-skilled experts in pharmaceutical technology.

The compounds of the present invention also encompass the solvates such as the hydrates.

Also the N-oxides on the tertiary nitrogen atoms are encompassed in the present invention.

The alkyl groups are straight or branched.

The $C_1$–$C_4$ alkyl group is preferably methyl, ethyl, n-propyl, iso-propyl, n-butyl, tert-butyl.

The $NR^5R^6$ group is preferably amino, methylamino, dimethylamino, diethylamino, pyrrolidinyl, piperidyl, 2-dimethylaminoethyl, 2-diethylaminoethyl.

Preferred examples of specific compounds according to the present invention are:
17β-(3-furyl)-14,15-seco-5β-androstan-3β,14β-diol
17β-(3-furyl)-14,15-seco-5β-androstan-3β,14β,15-triol
17β-(3-furyl)-14-oxo-14,15-seco-5β-androstan-3β-ol
3β-hydroxy-14-oxo-14,15-seco-5β-card-20(22)-enolide
3β,14β-dihydroxy-14,15-seco-5β-card-20(22)-enolide
3β-hydroxy-14-oxo-14,15-seco-5β-card-8,20(22)-dienolide
3β-hydroxy-14-oxo-14,15-seco-5β-card-20(22)-enolide-15-nitrile
3β,14β-dihydroxy-14,15-seco-5β-card-20(22)-enolide-15-nitrile
3β-hydroxy-14-oxo-14,15-seco-5β-card-20(22)enolide-15-(2-dimethylaminoethoxy-(E)-iminoethyl)
3β-hydroxy-14-oxo-14,15-seco-5β-card-20(22)-enolide-15-(2-dimethylaminoethoxy-(Z)-iminoethyl)
3β-hydroxy-14-oxo-14,15-seco-5β-card-20(22)-enolide-15-(E)-(guanidinoimino)

The invention further provides a process for the preparation of compounds of general formula (I) wherein R is 3-furyl, which comprises reducing the compounds having formula (I) wherein R is 2,5-dihydro-5-oxo-3-furyl, wherein the hydroxy groups are suitably protected e.g. in the form of tetrahydropiranyl ethers, tetrahydrofuranyl ethers, methoxymethyl ethers, ethoxyethyl ethers, silyl ethers such as as e.g. trimethylsilyl, t-butyldimethylsilyl, t-butyldiphenylsilyl. Other protective groups which are suitable under the chosen reduction conditions may be used.

The reduction reaction is best carried out in inert solvents such as e.g. diethyl ether, tetrahydrofurane, toluene, methylene chloride, hexane or mixtures thereof in the presence of a complex hydride such as diisobutyl aluminium hydride or 9-borabicyclo [3.3.1]nonane, at a temperature ranging from −78° C. to the boiling point of the afore-said solvents or their mixtures. During the work-up of the reaction mixture with diluted aqueous solutions of inorganic acids such as hydrochloric, sulfuric, phosphoric acid or organic acids such as acetic, tartaric, citric, oxalic acid, the protected hydroxy groups are deprotected thus giving the compounds having general formula (I).

The compounds of general formula (I) wherein R has the above-specified meaning and $R^2$ and $R^3$ are OH and H respectively, are obtained from the compounds of formula (I) wherein $R^2$ and $R^3$ taken together form a keto group and wherein the 3-hydroxy group is optionally protected as acetate by reduction with complex hydrides such as e.g. sodium borohydride, tri-t-butoxy lithiumaluminumhydride, sodium cyanoborohydride, in solvents such as e.g. dioxane, methanol, ethanol, tetrahydrofurane or a mixture of such solvents, optionally in the presence of water. To the reaction mixtures, acids such as e.g. hydrochloric acid, hydrobromic, acetic, sulfuric or bases such as e.g. sodium hydroxide or potassium hydroxide can be added to maintain the chosen pH.

The reaction is carried out at a temperature ranging from $-78°$ C. to room temperature. The reduction of the keto group gives a mixture of β/α epimers in variable proportions depending on the chosen reaction conditions. The β isomer is isolated from the mixture by crystallisation with suitable solvents such as e.g. ethyl acetate, ethanol, methanol, diethyl ether, hexane, cyclohexane or mixtures thereof, or by silica gel chromatography using e.g. ethyl acetate, diethyl ether, hexane, cyclohexane or mixture thereof as eluants.

The compounds of general formula (I) wherein $R^2$ and, $R^3$ are OH and H respectively and the 3-hydroxy group is selectively protected by a bulky group such as e.g. t-butyldimethylsilyl group, can be converted to other compounds of general formula (I) wherein $R^2$ and $R^3$ taken together form a keto group, by oxydation via conventional procedures such as e.g. with $CrO_3.2Py$ or $CrO_3$ and 2,5-dimethylpyrazole in pyridine or chlorinated solvents; thionyl chloride, oxalyl chloride or $Py.SO_3$ in DMSO in the presence of triethylamine; morpholine N-oxide and catalitic amounts of tetrapropylammonium perruthenate in the presence of molecular sieves, in chlorinated solvents and/or acetonitrile.

The compounds of general formula (I), wherein R is 2,5-dihydro-5-oxo-3-furyl, $R^1$ is CH=N—$R^4$, $R^2$ and $R^3$ taken together form a keto group and $R^4$ has the afore-said meanings, are obtained by condensation reaction of compounds of general formula (II) or (III).

$H_2NNHC(=NH)NR^5R^6$ (II)

$H_2NOR^7$ (III)

wherein $R^5$, $R^6$ and $R^7$ have the afore-said meanings, with ketoaldehyde (IV) which is a known compound (Cohnen E., Wedemeier K., Sinnwell V. (1982); Cardenolide, I. D-Ringspaltung von Cardenoliden, Liebigs Ann. Chem. 908-913).

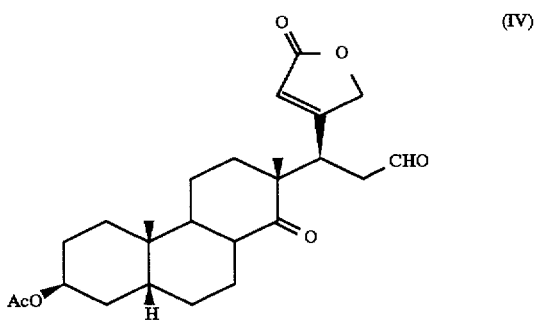

The compounds (II) and (III) can be used as free bases or as salts with an acid such as, e.g. hydrochloric, hydrobromic, hydriodic, carbonic, oxalic or sulfuric acid.

The reaction can be carried out in a solvent such as ethanol, methanol, acetonitrile, dioxane, tetrahydrofurane optionally in the presence of water or a mixture of the afore-said solvents, at a temperature ranging from 0° C. to the boiling point of the above-mentioned solvents or mixtures thereof. Additional salts such as e.g. $NaH_2PO_4$, $Na_2HPO_4$, NaOAc can be added to the reaction mixture; in order to maintain the chosen pH, acids such as e.g. hydrochloric, hydrobromic, sulfuric, phosphoric, or bases such as e.g. sodium hydroxide or potassium hydroxide can be added.

The 3-hydroxy group is deprotected by acid or basic hydrolysis at the end of the condensation reaction.

The compounds (II) and (III) are commercially available products and can be prepared by known methods.

All the afore-said conversion reactions are examples of well established organic chemistry procedures (see e.g.: J. March "Advanced Organic Chemistry", J. Wiley & Sons, 1985; D. Barton and W. D. Ollis "Comprehensive Organic Chemistry", Pergamon Press, 1979).

The compounds of general formula (I) prepared according to the present invention as well as their pharmacologically acceptable salts are useful agents for the treatment of cardiovascular disorders such as heart failure and hypertension.

The compounds of general formula (I) prepared according to the present invention as well as their pharmacologically acceptable salts have reduced toxicity compared with positive inotropic agents such as oubain and digitoxin.

The afore-mentioned compounds of general formula (I) show high activity and affinity for the $Na^+$, $K^+$-ATPase receptor site.

To test the affinity for the receptor site of the $Na^+$, $K^+$-ATPase and the agonist or inhibitory activity on the enzyme, the following tests were used:

a) displacement of the specific $^3$H-oubain binding from the $Na^+$, $K^+$-ATPase receptor purified according to Jorghensen (Jorghensen P., BBA, 1974, 356, 36) and Erdamnn (Erdmann E. et al., Arzneim. Forsh, 1984, 34, 1314);

b) inhibition of the activity of the purified $Na^+$, $K^+$-ATPase measured as % of hydrolysis of $^{32}$P-ATP in the presence and in the absence of the tested compound (Doucet A. et al., Am. J. Physiol., 1986, 251, F851).

Systolic blood pressure (SBP) and heart rate (HR) were measured by an indirect tail-cuff plethysmographic method in four-month old pre-hypertensive male rats, (MHS or SHR), i.e. before hypertension onset so as to register the basal value of SBP. The rats were then subdivided in groups of 7 animals each and the groups were divided in control and treated group. The compound, suspended in 0.5% (w/v) Methocel, was orally administered daily for at least five weeks. The control group received only Methocel.

SBP and HR were measured weekly, 6 and 24 hours after the treatment.

After five weeks of treatment, when the hypertension was fully developed in the control group (nine months old rats) a one-week wash-out was conducted in order to verify whether SBP would remain low or restored to the basal values of the control group.

The reliability of this method in assessing the hypotensive activity was previously tested on β-blocking agents which did not exhibit any hypotensive activity when administered to hypertensive rats (SHR), but were effective in preventing hypertension development if administered for more than five weeks following weaning (Takeda K. et al., Japan J. Pharmacol., 1979, 29,171; Takeda K. et al., Japan J. Pharmacol., 1982, 32, 283; Richer C. et al., Eur. J. Pharmacol., 1978, 47, 393).

The affinity for and the inhibitory activity on the enzyme of some compounds of the present invention are shown in the following table:

| COMPOUND | Binding ³H-oubain displacement −log IC$_{50}$ | Inhibitory activity −log IC$_{50}$ |
| --- | --- | --- |
| Comp. I-a | 6.2 | 5.2 |
| Comp. I-b | 6.0 | 5.0 |
| Comp. I-c | 5.2 | 4.3 |
| Comp. I-d | 6.7 | 5.6 |
| Comp. I-e | 6.9 | 5.1 |
| Comp. I-f | 6.1 | 5.1 |
| Comp. I-g | 6.5 | 5.5 |
| Comp. I-h | 7.0 | 6.0 |
| Comp. I-i | 5.6 | 4.0 |
| Comp. I-l | 5.4 | 4.2 |
| Comp. I-m | 5.5 | 4.1 |

The activity of some compounds in preventing the development of hypertension is shown in the following table:

EFFECT OF 5 WEEK TREATMENT IN SPONTANEOUS HYPERTENSIVE RATS (MHS) ON THE DEVELOPMENT OF HYPERTENSION.

| COMPOUND | RATS | DOSE* mg/kg/os | SBP mm Hg | HR beats/min. |
| --- | --- | --- | --- | --- |
| Controls | 7 | Methocel | 172+/−5.0 | 380+/−6.3 |
| Comp. I-a | 7 | 20 | 155+/−4.3 | 370+/−10.5 |
| Comp. I-d | 7 | 20 | 156+/−4.6 | 383+/−11.4 |
| Comp. I-h | 7 | 20 | 160+/−7.8 | 377+/−10.5 |

*In 0.5% W/V Methocel

The following examples illustrate the invention without limiting it.

EXAMPLE 1

17β-(3-furyl)-14,15-seco-5β-androstan-3β,14β-diol (I-a)

To a solution of 0.54 g of 3β,14β-dihydroxy-14,15-seco-5β-card-20(22)-enolide (I-e) in THF (13 ml), 1.9 g of imidazole and 1.78 ml of trimethylchlorosilane were added. After 1 hour the reaction mixture was poured in water, the suspension thus formed was extracted with EtOAc, the organic phase was separated, washed with a saturated solution of NaCl and dehydrated on anhydrous Na$_2$SO$_4$; the solvent was removed by evaporation under reduced pressure, 716 mg of disilyl ether were obtained as a white foam; the product was used without further purification in the following step.

The disilyl ether was dissolved in anhydrous THF (10 ml) and at the solution, maintained at −50° C., 7 ml (1M in hexane) of DIBAL-H were added over 30 min in a nitrogen atmosphere. After one hour, 16 ml of a saturated solution of NaH$_2$PO$_4$ were slowly added while keeping the temperature below −20° C.; then the reaction mixture was brought to room temperature, the solid obtained was filtered off, washed with EtOAc and eliminated; the aqueous filtrate was extracted with the EtOAc used to wash the solid. The organic phase was separated and washed with a saturated solution of NaHCO$_3$, then with a saturated solution of NaCl and dehydrated on anhydrous Na$_2$SO$_4$. The solvent was then removed by evaporation under reduced pressure. The crude product (intermediate α,β-unsaturated lactole) was dissolved in THF (22 ml) and then treated with 1N H$_2$SO$_4$ (22 ml) at room temperature for 30 minutes. The reaction mixture was neutralized by adding solid NaHCO$_3$, the organic solvent was evaporated under reduced pressure and the remaining aqueous suspension was extracted with CH$_2$Cl$_2$. The organic phase was separated, washed with a saturated solution of NaCl and dehydrated on anhydrous Na$_2$SO$_4$; the solvent was removed by evaporation under reduced pressure. The crude product thus obtained was purified by silica gel chromatography, using cyclohexane/EtOAc (70:30 v/v) as eluant; 0.31 g of the compound (I-a) as a white solid were obtained.

$^1$H-NMR(300 MHz, CDCl$_3$, ppm from TMS): 0.75(3H,t); 0.93(3H,s);1.00(3H, s); 2.62(1H,dd); 2.81(1H,d); 4.08(1H, bs); 6.30(1H,bs); 7.26(1H,bs); 7.39(1H,bt).

EXAMPLE 2

17β-(3-furyl)-14,15-seco-5β-androstan-3β,14β,15-triol (I-b)

The compound (I-b) (0.25 g) was obtained as a white solid starting from 0.45 g of 3β,14β,15-trihydroxy-14,15-seco-β-card-20(22)enolide (Cohnen E., Wedemeier K., Sinnwell V. (1982). Cardenolide I. D-Ringspaltung von Cadenoliden. Liebigs Ann. Chem. 908–913), using the procedure described in Ex. 1.

$^1$H-NMR(300 MHz,CDCl$_3$,ppm from TMS): 0.96(3H,s); 1.03(3H,s); 2.81(1H,d); 2.94(1H,dd); 3.45(1H,m); 3.55(1H, m); 4.08(1H,bs); 6.37 (1H,bs); 7.00(1H,bs); 7.41(1H,bt).

EXAMPLE 3

17β-(3-furyl)-14-oxo-14,15-seco-5β-androstan-3β-ol (I-c)

To a solution of 332 mg of 17β-(3-furyl)-14,15-seco-5β-androstan-3β,14β-diol (I-a) in DMF (5 ml) maintained at 0° C., 634 mg, (9.3 mM) of imidazole and 980 mg of t-butyldimethylcholorosilane were added; the reaction mixture was brought to room temperature and stirred for 19 hours. The reaction mixture was diluted with water and extracted with CH$_2$Cl$_2$. The organic phase was separated, washed with a saturated solution of NaCl and dehydrated on anhydrous Na$_2$SO$_4$; the solvent was removed under reduced pressure to give 384 mg of 3-silyl derivative as a colourless oil, which was used as such in the following step.

The silyl ether was dissolved in 12 ml of CH$_2$Cl$_2$ and 200 mg of powdered 4 Å molecular sieves, 285 mg of morpholine N-oxide and 17 mg of tetrapropylammonium perruthenate were added to the solution in sequence. After 24 hours under vigorous stirring, the reaction mixture was filtered on a layer of silica gel, using cyclohexane/EtOAc (97/3 v/v) as eluant. 0.32 g of 3-silyl ether of (I-c) as colourless oil were obtained.

Such product was deprotected by dissolving it in CHCl$_3$/MeOH (7.5 ml/15 ml) and adding a drop of concentrated HCl. After 21 hours the reaction mixture was neutralized with a saturated solution of NaHCO$_3$, the organic solvent was evaporated under reduced pressure and the resulting aqueous suspension was extracted with EtOAc; the organic phase was washed with water, dehydrated on anhydrous Na$_2$SO$_4$ and the solvent was removed by evaporation under reduced pressure. The crude product was purified on a silica gel column using cyclohexane/EtOAc (75:25 v/v) as eluant; 0.20 g of the compound (I-c) as a white solid were obtained.

$^1$H-NMR(300 MHz, CDCl$_3$,ppm from TMS): 0.81(3H,t); 1.01(3H,s); 1.20(3H, s); 2.62(1H,m); 2.78(1H,dd); 4.09(1H, bs); 6.25(1H,bs); 7.17(1H,bs); 7.34(1H,bt).

EXAMPLE 4

3β-hydroxy-14-oxo-14,15-seco-5β-card-20(22)-enolide (I-d)

To a solution of 5 g of 3β-acetoxy-14,15-dioxo-14,15-seco-5β-card-20(22)-enolide in CH$_2$Cl$_2$ (50 ml) (IV) (Cohnen E., Wedemeier K., Sinnwell V. (1982). Cardenolide, I. D-Ringspaltung von Cardenoliden. Liebigs Ann. Chem. 908–913) 1.6 ml of 1,2-ethaneditiol and 1.25 ml of BF$_3$.Et$_2$O were added; an instantaneous reaction took place. After about 10 minutes the reaction mixture was poured in a saturated solution of NaHCO$_3$, the organic phase was separated, washed with water, dehydrated on Na$_2$SO$_4$ and the solvent removed under reduced pressure. The crude product was dissolved in 96% EtOH to which a large excess of nickel Raney was added. The reaction mixture was kept at the reflux temperature for two hours, the solid filtered off and the solvent removed under reduced pressure to give the 3-acetate derivative of (I-d). The crude 3-acetate was dissolved in MeOH and treated with an aqueous solution of 5% HCl at room temperature for 48 hours; the reaction mixture was then neutralized with a saturated solution of NaHCO$_3$, the organic solvent was evaporated under reduced pressure and the resulting aqueous suspension extracted with EtOAc; the organic phase was washed with water, dehydrated on anhydrous Na$_2$SO$_4$ and the solvent evaporated under reduced pressure. The crude product was purified on a silica gel column using hexane/EtOAc (70:30 v/v) as eluant; 3.2 g of the compound (I-d) as a white solid were obtained.

$^1$H-NMR(300 MHz,CDCl$_3$,ppm from TMS): 0.89(3H,t); 1.03(3H,s); 1.23(3H,s); 2.57(2H,m); 4.13(1H,bs); 4.70(1H, dd); 4.94(1H,dd) 5.86(1H,bt).

EXAMPLE 5

3β,14β-dihydroxy-14,15-seco-5β-card-20(22)-enolide (I-e)

To a solution of 7.0 g of 3β-hydroxy-14-oxo-14,15-seco-5β-card-20(22)-enolide (I-d) in MeOH (600 ml) kept at −30° C., 1.6 g of NaBH$_4$ were added; after 12 hours the reaction mixture was treated with an aqueous solution of 10% HOAc, brought to room temperature and diluted with a saturated solution of NaCl. The organic solvent was evaporated under reduced pressure leaving an aqueous suspension which was extracted with CHCl$_3$. The organic phase was separated, washed with a saturated solution of NaCl, dehydrated on anhydrous Na$_2$SO$_4$ and the solvent evaporated under reduced pressure. The crude product was purified on a silica gel column using EtOAc/ciclohexane (70:30 v/v) as eluant. 1.8 g of the compound (I-e) as a white solid and 3.6 g of 3β,14α-dihydroxy-14,15-seco-5β-card-20(22)-enolide were obtained.

(I-e) 1H-NMR(300 MHz,CDCl$_3$,ppm from TMS): 0.86 (3H,t); 0.94(3H,s); 1.02(3H,s); 2.50(1H,dd); 2.75(1H,m); 4.15(1H,bs); 4.72(1H,dd); 4.97(1H,dd); 5.90(1H,bt).

EXAMPLE 6

3β-hydroxy-14-oxo-14,15-seco-5β-card-8,20(22)-dienolide (I-f)

To a solution of 770 mg of 3β-acetoxy-14-oxo-14,15-seco-5β-card-20(22)-enolide (I-d 3-acetate) obtained as described in ex. 4 in THF (23 ml) 0.9 g of pyridinium bromide perbromide were added and the reaction mixture was stirred at room temperature for 18 hours. The reaction mixture was then poured in water and extracted with EtOAc; the organic phase was separated and washed with HCl 1N and then with a saturated solution of NaCl. The solvent was removed by evaporation under reduced pressure. The oily residue was heated at 70° C. for 30 minutes and purified by silica gel chromatography using ciclohexane/CH$_2$Cl$_2$/EtOAc (3:2:1 v/v/v) as eluant; obtaining 400 mg of (I-f 3-acetate) which was deprotected by the method described in ex. 4; 200 mg of the compound (I-f) as a white solid were obtained.

1H-NMR(300 MHz,CDCl$_3$, ppm from TMS): 0.88(3H,t); 1.14(3H,s); 1.17(3H,s); 2.76(1H,dd); 3.92(1H,bs); 4.74(1H, dd); 4.78(1H,dd); 5.83(1H,bt).

EXAMPLE 7

3β-hydroxy-14-oxo-14,15-seco-5β-card-20(22)-enolide-15-nitrile (Ig)

To a solution of 2.0 g of 3β-acetoxy-14-oxo-14,15-seco-5β-card-20(22)-enolide-15-carboxylic acid (Cohnen E., Wedemeier K., SinnwellV. (1982). Cardenolide, I. D-Ringspaltung von Cardenoliden. Liebigs Ann. Cehm. 908–913) in dioxane (30 ml), 4.0 ml of SOCl$_2$ were added and the reaction mixture was heated at 50° C. for 2 hours. Afterwards the temperture was raised to 100° C. and a nitrogen stream was bubbled in the reaction mixture to remove the solvent and the excess of reagent. The residue was dissolved in dioxane (30 ml), and the reaction mixture was cooled to 0° C. At this time, gaseous NH$_3$ was bubbled in the solution for 30 minutes; the temperature of the reaction mixture was raised to room temperature, and after one hour 10 ml of CH$_2$Cl$_2$ were added to the mixture. The solid precipitate which formed was filtered off and the solvent evaporated under reduced pressure; 2.5 g of an amide were obtained which was used in the following step without being further purified.

The amide was dissolved in 30 ml of pyridine and 0.82 ml of POCl$_3$ were added to the resulting solution. The reaction mixture was heated at 60° C. for 24 hours and then poured into a mixture of 1N HCl and ice. The suspension thus obtained was extracted with CH$_2$Cl$_2$, the organic phase was separated, washed with water, dehydrated on anhydrous Na$_2$SO$_4$ and the solvent was evaporated under reduced pressure; the residue obtained was treated with diluted acid as described in Ex. 4 and purified by silica gel chromatography using CH$_2$Cl$_2$/EtOAc (50:50 v/v) as eluant; 0.5 g of compound (I-g) as a white solid were obtained.

$^1$H-NMR(300 MHz,CDCl$_3$, ppm from TMS): 1.05(3H,s); 1.27(3H,s); 2.59(1H,dt); 2.65(1H,dd); 2.83(1H,dd); 3.10 (1H,dd); 4.13(1H,bs); 4.80(1H,dd); 4.88(1H,dd); 6.09(1H, bs).

EXAMPLE 8

3β,14β-dihydroxy-14,15-seco-5β-card-20(22)-enolide-15-nitrile (I-h)

To a solution of 1.66 g of 3β-hydroxy-14-oxo-14,15-seco-5β-card-20(22)-enolide-15-nitrile (I-g) in MeOH (135 ml) kept at −30° C.; 240 mg of NaBH$_4$ were added; one hour later, 10 ml of a solution of 10% HOAc were added to the reaction mixture, the temperature was allowed to rise to room temperature and the mixture was diluted with a saturated solution of NaCl. The organic solvent was evaporated under reduced pressure and the resultant suspension was extracted with CH$_2$Cl$_2$; the organic phase was separated, washed with water, dehydrated on anhydrous Na$_2$SO$_4$ and the solvent was evaporated under reduced pressure. The crude product was purified by silica gel chromatography using CH$_2$Cl$_2$/EtOAc (50:50 v/v) as eluant. 0.38 g of the compound (I-h) as a white solid and 0.42 g of 3β,14α-dihydroxy-14,15-seco-5β-card-20(22)-enolide-15-nitrile were obtained.

(I-h) $^1$H-NMR(300 MHz,CDCl$_3$/CD$_3$OD, ppm from TMS): 0.89 (3H,s); 0.99(3H,s); 2.49(1H,dd); 2.72(1H,dd); 2.81(1H,dd); 3.05(1H,dd); 4.07(1H,bs); 4.80(1H, dd); 4.98 (1H,dd); 6.02(1H,bs).

EXAMPLE 9

3β-hydroxy-14-oxo-14,15-seco-5β-card-20(22)-enolide-15-(2-dimethylaminoethoxy-(E)-imino) (I-i) and 3β-hydroxy-14-oxo-14,15-seco-5β-card-20(22)-enolide-15(2-dimethylaminoethoxy-(Z)-imino) (I-l)

A solution of 0.5 g of 3β-acetoxy-14,15-dioxo-14,15-seco-5β-card-20(22)-enolide (IV) (Cohnen E., Wedemeier K., Sinnwell V. (1982). Cardenolide, I. D-Ringspaltung von Cardenoliden. Liebigs Ann. Chem. 908–913), 0.2 g of sodium acetate and 0.42 g of 2-dimethylaminoethoxyamine dichlorohydrate, in 70 ml of 96% ethanol was heated at 50° C. for two hours. The organic solvent was removed by evaporation under reduced pressure and the residue was extracted with $CH_2Cl_2$ and water. The organic phase was separated, washed with water, dehydrated on anhydrous $Na_2SO_4$ and the solvent evaporated under reduced pressure. The crude residue was dissolved in methanol (100 ml) and hydrolyzed in an acid environment as described in Ex. 4. After purification on a silica gel column using $CH_2Cl_2$/MeOH (90/10 v/v) as eluant; 0.15 g of the compound (I-i) as a white foam and 0.18 g of compound (I-l) as a yellowish foam were obtained.

(I-i) $^1$H-NMR(300 MHz, $CDCl_3$,ppm from TMS):1.05 (3H,s); 1.28(3H, s); 2.27(3H,s); 2.35–3.10(6H,m); 4.08(2H, t); 4.14(1H,m); 4.25–4.95(2H,m); 5.91(1H,m); 7.36(1H,dd).

(I-l) $^1$H-NMR(300 MHz,$CDCl_3$,ppm from TMS):1.05 (3H,s); 1.28(3H,s); 2.31(3H,s); 2.35–3.07(6H,m); 4.14(1H, m); 4.16(2H,t); 4.68–4.90(2H,m); 5.91(1H,m); 6.57(1H,dd).

EXAMPLE 10

3β-hydroxy-14-oxo-14,15-seco-5β-card-20(22)enolide-15-(E)-(guanidinoimino) (I-m)

To a solution of 0.5 g of 3β-acethoxy-14,15-dioxo-14,15-seco-5β-card-20(22)-enolide (IV) (Cohnen E., Wedemeier K., Sinnwell V. (1982). Cardenolide, I. D-Ringspaltung von Cardenoliden. Liebigs Ann. Chem. 908–913) in 25 ml of a mixture (1:1 v/v) of dioxane and water, 0.19 g of aminoguanidine bicarbonate dissolved in 10 ml of the same solvent mixture were added. The reaction mixture was heated at the reflux temperature for one hour and the organic solvent was removed by evaporation under reduced pressure. The aqueous suspension thus obtained was extracted with a (9:1 v/v) mixture of $CHCl_3$/MeOH; the organic phase was separated, washed with a saturated solution of NaCl, dehydrated on anhydrous $Na_2SO_4$ and the solvent was removed by evaporation under reduced pressure. The residue thus obtained was treated with diluted acid as described in Ex. 4 and purified by silica gel chromatography using $CHCl_3$/MeOH/$NH_4OH$ (80/20/2 v/v/v) as eluant. 0.15 g of the title compound were obtained as a white solid.

$^1$H-NMR(300 MHz,DMSO-$D_6$,ppm from TMS): 0.99 (3H,s); 1.19(3H, s); 2.01(3H,s); 2.30–2.70(3H,m); 3.18(1H, dd); 4.81(2H,m); 4.91(1H,m); 5.40–5.91(4H,bb); 6.02(1H, s); 7.23(1H,dd).

We claim:

1. Seco-D steroids of formula (I)

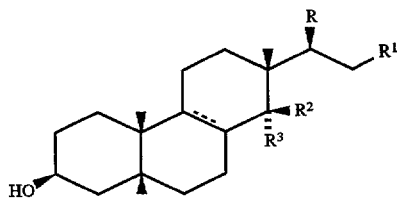

(I)

wherein:

R is 3-furyl or 2,5-dihydro-5-oxo-3-furyl;

when R is 3-furyl the symbol ---- represents a single bond;

$R^1$ is methyl or hydroxymethyl;

$R^2$ and $R^3$ are OH and H respectively, or taken together form a keto group:

with the proviso that when $R^2$ and $R^3$ taken together form a keto group, $R^1$ is methyl;

when R is 2,5-dihydro-5-oxo-3-furyl the symbol ---- represents either a single or a double bond;

$R^1$ is methyl, cyano or CH=N~ $R^4$;

$R^2$ and $R^3$ have the above-specified meaning;

with the proviso that when $R^1$ is CH=N~ $R^4$, $R^2$ and $R^3$ taken together form a keto group;

with the proviso that when the symbol ---- represents a double bond, $R^1$ is methyl, and $R^2$, $R^3$ taken together form a keto group;

the symbol ~ represents either the Z or the E isomer;

$R^4$ is NHC(=NH)$NR^5R^6$ or $OR^7$;

wherein $R^5$, $R^6$, equal or different, are H or $C_1$–$C_4$ alkyl; or $R^5$, $R^6$ taken together can possibly form, with the heteroatom they are linked to, a five- or six-membered monoheterocyclic ring;

$R^7$ is H, $CH_3$, $C_2$–$C_6$ alkyl, unsubstituted or substituted by $NR^8R^9$;

wherein $R^8$ and $R^9$, equal or different, are H or $C_1$–$C_4$ alkyl;

and the pharmaceutically acceptable salts thereof.

2. A compound according to claim 1, which is selected from:

17β-(3-furyl)-14,15-seco-5β-androstan-3β,14β-diol

17β-(3-furyl)-14,15-seco-5β-androstan-3β,14β,15-triol

3β-hydroxy-17β-(3-furyl)-14,15-seco-5β-androstan-14-one

3β-hydroxy-14-oxo-14,15-seco-5β-card-20(22)-enolide

3β,14β-dihydroxy-14,15-seco-5β-card-20(22)-enolide

3β-hydroxy-14-oxo-14,15-seco-5β-card-8.20(22)-dienolide

3β-hydroxy-14-oxo-14,15-seco-5β-card-20(22)-enolide-15-nitrile

3β,14β-dihydroxy-14,15-seco-5β-card-20(22)-enolide-15-nitrile

3β-hydroxy-14-oxo-14,15-seco-5β-card-20(22)-enolide-15-(2-(dimethylaminoethoxy-(E)-imino)

3β-hydroxy-14-oxo-14,15-seco-5β-card-20(22)-enolide-15-(2-dimethylaminoethoxy-(Z)-imino 3β-hydroxy-14-oxo-14,15-seco-5β-card-20(22)-enolide-15-(E)-(guanidinimino).

3. A pharmaceutical composition comprising a compound according to claim 1 of formula (I) and a pharmaceutically acceptable carrier therefor.

* * * * *